(12) United States Patent
Sato et al.

(10) Patent No.: US 7,973,053 B2
(45) Date of Patent: Jul. 5, 2011

(54) NERVE CELL DEATH INHIBITOR

(75) Inventors: Fumiyasu Sato, Higashimurayama (JP);
Yasunobu Yoshinaka,
Higashimurayama (JP); Taro Aoki,
Higashimurayama (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 0 days.

(21) Appl. No.: 12/676,265

(22) PCT Filed: Oct. 2, 2008

(86) PCT No.: PCT/JP2008/002768
§ 371 (c)(1),
(2), (4) Date: Mar. 3, 2010

(87) PCT Pub. No.: WO2009/044547
PCT Pub. Date: Apr. 9, 2009

(65) Prior Publication Data
US 2010/0173938 A1 Jul. 8, 2010

(30) Foreign Application Priority Data
Oct. 3, 2007 (JP) ................................ 2007-259682

(51) Int. Cl.
*A61K 31/47* (2006.01)
(52) U.S. Cl. ...................................................... 514/311
(58) Field of Classification Search .................... 514/311
See application file for complete search history.

(56) References Cited

U.S. PATENT DOCUMENTS

| | | | |
|---|---|---|---|
| 6,080,778 A | 6/2000 | Yankner et al. | |
| 6,440,387 B1 | 8/2002 | Yankner et al. | |
| 6,472,421 B1 | 10/2002 | Wolozin | |
| 2005/0215620 A1 | 9/2005 | Friedhoff | |
| 2007/0110715 A1* | 5/2007 | Grimaldi | 424/85.6 |

FOREIGN PATENT DOCUMENTS

| | | |
|---|---|---|
| JP | 2002-529500 A | 9/2002 |
| WO | 99/48488 A2 | 9/1999 |
| WO | 00/28981 A2 | 5/2000 |
| WO | 01/32161 A2 | 5/2001 |
| WO | 01/96311 A2 | 12/2001 |
| WO | 02/062824 A2 | 8/2002 |
| WO | 03/082298 A1 | 10/2003 |
| WO | 2005/063294 A1 | 7/2005 |
| WO | 2005/099823 A1 | 10/2005 |
| WO | 2007/088705 A1 | 8/2007 |

OTHER PUBLICATIONS

T. Miida et al, "Prevention of stroke and dementia by statin therapy: experimental and clinical evidence of their pleiotropic effects", Parmacol Ther, 2007, vol. 113, No. 2, pp. 378-393.
C. Oki et al, "Anti-Oxidative Effect of Pitavastatin against Ischemic Brain Damage", Therapeutic Research, 2005, vol. 26, No. 6 pp. 1277-1286.
B. Wolozin et al, "Decreased Prevalence of Alzheimer Disease Associated with 3-Hydroxy-3-Methyglutaryl Coenzyme A Reductase Inhibitors," Arch Neurol, Oct. 2000, vol. 57, pp. 1439-1443.
S. Akasofu et al, "Protective Effect of Donepezil in a Primary Culture of Rat Cortical Neurons Exposed to Oxygen-Glucose Deprivation," European Journal of Pharmacology, 2003, No. 472, pp. 57-63.
J.T. Coyle et al, "Alzheimer's Disease: A Disorder of Cortical Cholinergic Innervation" Science, Mar. 11, 1983, vol. 219, pp. 1184-1190.
P. Doerfler et al, "Presenilin-dependent Gamma-Secretase Activity Modules Thymocyte Development," PNAS, Jul. 31, 2001, vol. 98, No. 16, pp. 9312-9317.
J.A. Hardy et al, "Alzheirmer's Disease: The Amyloid Cascade Hypothesis," Science, Apr. 10, 1992, vol. 256, pp. 184-185.
T. Hayashi et al, "HMG CoA Reductase Inhibitors Reduce Ischemic Brain Injury of Wistar Rats Through Decreasing Oxidative Stress on Neurons," Brain Research, 2005, No. 1037, pp. 52-58.
A. Svensson et al, "Tacrine and Donepezil Attenuate the Neurotoxic Effect of ABeta(25-35) in Rat PC12 Cells," NeuroReport, May 11, 1998, vol. 9, No. 7, pp. 1519-1522.
Y. Takada et al, "Nicotinic Acetylcholine Receptor-Mediated Neuroprotection by Donepezil Against Glutamate Neurotoxicity in Rat Cortical Neurons," Journal of Pharmacology and Experimental Therapeutics, 2003, vol. 306, No. 2, pp. 772-777.
International Search Report of PCT/JP2008/002768, mailing date of Nov. 11, 2008.
Notification of Transmittal of Translation of the International Preliminary Report on Patentability (Form PCT/IB/338) of International Application No. PCT/JP2008/002768 mailed May 14, 2010, with Forms PCT/IB/373 and PCT/ISA/237.
Supplementary European Search Report dated Dec. 17, 2010, issued in corresponding European Patent Application No. 08 83 6702.
Kumagai, R. et al.; "Pitavastatin, a 3-hydroxy-3-methylglutaryl-coenzyme A (HMG-CoA) reductase inhibitor, reduces hippocampal damage after transient cerebral ischemia in gerbils"; Journal of Neural Transmission, vol. 111, No. 9, Sep. 2004, pp. 1103-1120, XP002614678.
Roman, G et al.; "Efficacy and safety of donepezil in vascular dementia: results from the largest double-blind trial in vascular dementia patients"; European Neuropsychopharmacology, vol. 16, No. Suppl. 4, Sep. 2006, pp. S481-S482, XP002614677, & 19th Congress of the European—Collage—of—Neuropsychopharmacology; Paris, France, Sep. 16-20, 2006.
Tounai, Hiroko et al.; "Immunohistochemical Study on Distribution of NF-[kappa] B and p53 in Gerbil Hippocampus after Transient Cerebral Ischemia: Effect of Pitavastatin"; Metabolic Brain Disease, Klumer Academic Publishers-Plenum Publishers, NE, vol. 22, No. 1, Jan. 17, 2007, pp. 89-104, XP019482818.

* cited by examiner

*Primary Examiner* — Jennifer M Kim
(74) *Attorney, Agent, or Firm* — Westerman, Hattori, Daniels & Adrian, LLP

(57) ABSTRACT

The present invention provides a medicament exhibiting an excellent nerve cell death inhibitory action.
The present invention relates to a nerve cell death inhibitor comprising a pitavastatin and donepezil or a salt thereof in combination.

19 Claims, 2 Drawing Sheets

[FIG 1]
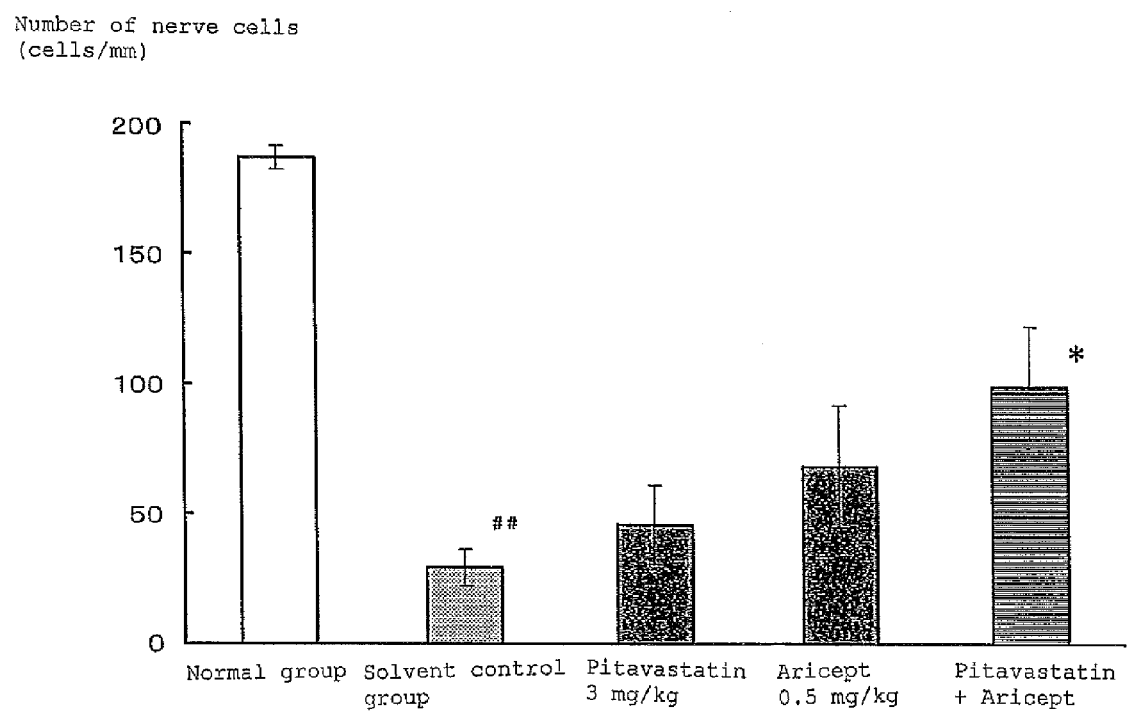

[FIG 2]
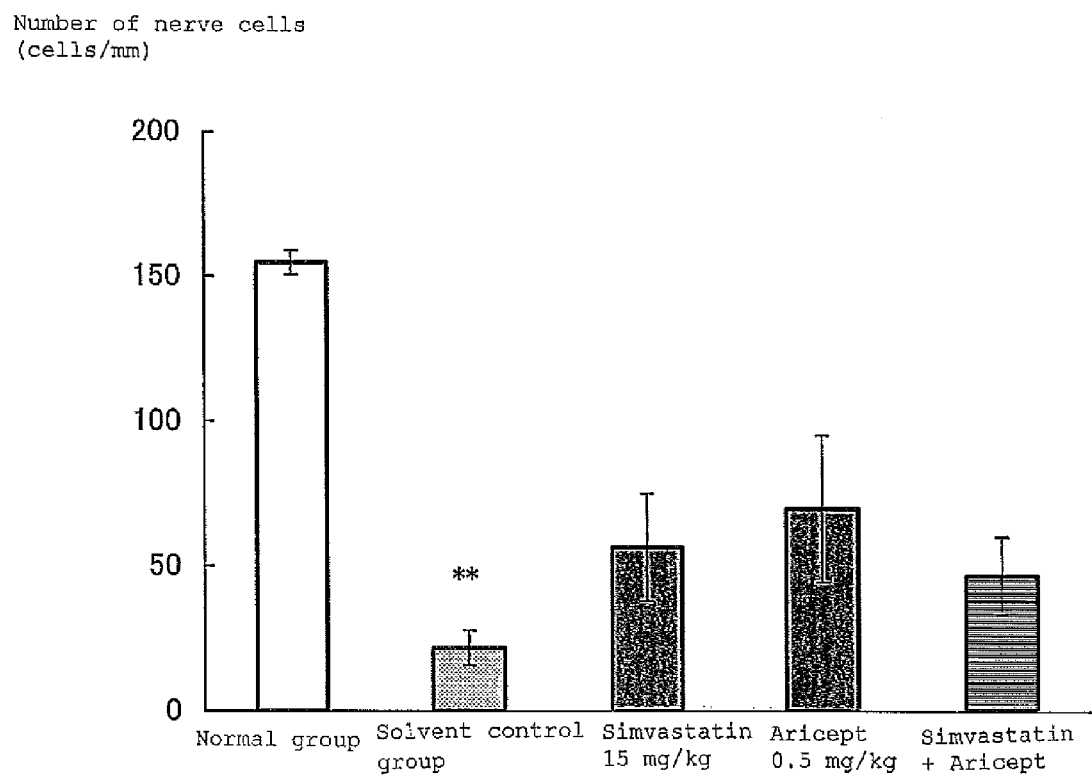

NERVE CELL DEATH INHIBITOR

TECHNICAL FIELD

The present invention relates to a nerve cell death inhibitor, and particularly, to a cerebral nerve protective agent having a nerve cell death inhibitory action. More particularly, the present invention relates to a progression inhibitor for a demential disease such as degenerative dementia, which is represented by vascular dementia or Alzheimer type dementia; a prophylactic and/or therapeutic agent for demential diseases such as degenerative dementia, which is represented by vascular dementia or Alzheimer type dementia; a prophylactic agent against the recurrence of cerebral infarction; or a prophylactic and/or therapeutic agent for cerebral infarction, the agent having a nerve cell death inhibitory action.

BACKGROUND ART

Along with the dynamics of population aging, an increase in the number of patients in a state of lowered cognitive function, that is, patients having a demential disease, poses a social problem. The demential disease is defined as "a state in which memory function and other cognitive functions have been deteriorated to the extent that the everyday life is interfered with, by the organic changes occurring in the brain as a result of cerebrovascular diseases, Alzheimer's disease and other factors."

Dementia is largely classified into vascular dementia and degenerative dementia based on the cause, but all of them result in falling off of nerve cells. Under the current situation where no effective methods for recovery therefrom are known, the inhibition of disease progression will be the primary goal.

Known as one type of degenerative dementia, Alzheimer type dementia is estimated to affect approximately 18 million patients over the world, the number being anticipated to further increase in the future, and the development of a method for prevention or a method for treatment is expected. As pathological features of Alzheimer type dementia, cerebral tissue atrophy and emergence of senile plaque in the cerebral cortex may be mentioned, and it is found that senile plaque is associated with deposition of β-amyloid.

As a method for treating Alzheimer type dementia, there is known development of a new drug based on the cholinergic hypothesis (Non-Patent Document 1), or a new drug based on the amyloid cascade hypothesis (Non-Patent Document 2).

Among them, the cholinergic hypothesis is based on the fact that the acetylcholine synthetase activity is specifically reduced in the cerebral cortex of Alzheimer type dementia patients, and the hypothesis is associated with a perspective that supplementation of the amount of acetylcholine by any means will lead to the treatment. As a therapeutic agent based on this hypothesis, donepezil hydrochloride which has an inhibitory action against acetylcholinesterase, an acetylcholine degrading enzyme, has been created, and is producing certain effects. However, since the drug based on the cholinergic hypothesis is targeted to the reinforcement of neural circuitry, there are limits on the effectiveness of the drug in regard to the fact that nerve cells keep on falling off, along with the progress of the disease condition.

On the other hand, the amyloid cascade hypothesis is associated with a perspective that aggregation and deposition of β-amyloid bring about changes in neurofibrils, eventually causing nerve cell death, and prevention of the β-amyloid deposition will lead to the treatment. As a therapeutic drug based on this hypothesis, development of an inhibitor against γ-secretase, a vaccine and the like is being anticipated, but due to the problems of adverse side effects, marketing thereof has not yet been achieved (Non-Patent Document 3).

As another approach, based on the report of epidemiological data showing that patients taking a HMG-CoA reductase inhibitor (hereinafter, may also be referred to as a statin), which is a therapeutic agent for hyperlipidemia, exhibit a low morbidity rate for Alzheimer type dementia (Non-Patent Document 4), or the finding that statins decrease the production of β-amyloid, a possibility of utilizing statins as a therapeutic agent for Alzheimer type dementia has been reported (Patent Documents 1 to 8). It has been also reported that statins have an inhibitory action against the formation of active γ-secretase complexes (Patent Document 9).

The following reports are found in regard to the action of the above-mentioned drugs on nerve cell death. Specifically, donepezil hydrochloride is known to have a protective action against the neurotoxicity of β-amyloid or glutamic acid (Non-Patent Documents 5 and 6), or a nerve cell protective action in an ischemic model (Non-Patent Document 7). However, all of these represent results obtained in vitro, and since the concentration exhibiting a nerve protective action requires a higher dose than the concentration exhibiting an acetylcholinesterase inhibitory action, it is not certain as to whether the nerve cell protective action is manifested in patients administered with the drug, or not.

Furthermore, in the case of statins, a statin suppresses an increase in the size of cerebral infarction in an animal model of transient cerebral ischemia is reported (Non-Patent Document 8), and a statin exhibits a nerve cell protective action through a suppressive action on superoxide dismutase reduction is known (Non-Patent Document 9).

Also known is a report that an acetylcholinesterase inhibitor such as donepezil hydrochloride and a statin are combined and applied to Alzheimer type dementia (Patent Document 10). However, this document does not present any specific data, and it is not certain of specifically what combination of drugs would be optimal. In addition to that, there are known clinical results obtained by using galantamine which is an acetylcholinesterase inhibitor, and a statin in combination, and it is pointed out that in the case of combined treatment, the risk of adverse side effects is increased in comparison to the case of single drug treatment (Patent Document 11). However, it is not reported that donepezil hydrochloride has a nerve protective action against transient cerebral ischemia.

As discussed so far, a drug satisfactorily having an effective nerve cell death inhibitory action against demential diseases including Alzheimer type dementia, does not yet exist, and it is desired to provide such a drug. Furthermore, a drug having an effective nerve cell death inhibitory action is also useful as a prophylactic agent against the recurrence of cerebral infarction, and therefore a prophylactic and/or therapeutic agent for cerebral infarction, in addition to demential diseases.

[Patent Document 1] WO 02/062824
[Patent Document 2] WO 01/096311
[Patent Document 3] WO 01/032161
[Patent Document 4] WO 00/028981
[Patent Document 5] WO 99/048488
[Patent Document 6] U.S. Pat. No. 6,472,421
[Patent Document 7] U.S. Pat. No. 6,440,387
[Patent Document 8] U.S. Pat. No. 6,080,778
[Patent Document 9] WO 2005/063294
[Patent Document 10] WO 2005/099823
[Patent Document 11] WO 03/082298
[Non-Patent Document 1] Science, 219:1184-1190, 1983
[Non-Patent Document 2] Science, 256:184-185, 1992

[Non-Patent Document 3] Proc. Natl. Acad. Sci. USA, 98:9312-9317, 2001

[Non-Patent Document 4] Arch. Neurol., 57:1439-1443, 2000

[Non-Patent Document 5] Neuroreport, 9:1519-1522, 1998

[Non-Patent Document 6] J. Pharmacol. Exp. Ther., 306:772-777, 2003

[Non-Patent Document 7] Eur. J. Pharmacol., 472:57-63, 2003

[Non-Patent Document 8] Brain Research, 1037:52-58, 2005

[Non-Patent Document 9] Therapeutic Research, 26:1277-1286, 2005

DISCLOSURE OF THE INVENTION

Problems to be Solved by the Invention

The present invention is to provide a drug exhibiting an excellent nerve cell death inhibitory action.

Means for Solving the Problems

Under such circumstances, the inventors of the present invention devotedly carried out investigations, and as a result, they surprisingly found that when a pitavastatin such as pitavastatin calcium, and donepezil or a salt thereof are used in combination, a conspicuous nerve cell death inhibitory action specific to this combination is obtainable, thus completing the present invention. To the present, there has been no report on to what degree the nerve cell death inhibitory action would be manifested in an example of combining a pitavastatin and donepezil or a salt thereof.

Specifically, the present invention provides the following:

(1) A nerve cell death inhibitor comprising a pitavastatin and donepezil or a salt thereof in combination;

(2) The nerve cell death inhibitor according to (1), wherein the pitavastatin is pitavastatin calcium;

(3) The nerve cell death inhibitor according to (1) or (2), wherein the salt of donepezil is donepezil hydrochloride;

(4) The nerve cell death inhibitor according to any one of (1) to (3), wherein a preparation containing a pitavastatin and a preparation containing donepezil or a salt thereof are administered in combination;

(5) The nerve cell death inhibitor according to any one of (1) to (4), wherein the nerve cell death inhibitor is a cerebral nerve protective agent;

(6) The nerve cell death inhibitor according to any one of (1) to (4), wherein the nerve cell death inhibitor is a prophylactic and/or therapeutic agent for a demential disease;

(7) The nerve cell death inhibitor according to (6), wherein the prophylactic and/or therapeutic agent for a demential disease is a progression inhibitor for a demential disease;

(8) The nerve cell death inhibitor according to (6) or (7), wherein the demential disease is vascular dementia or degenerative dementia;

(9) The nerve cell death inhibitor according to (8), wherein the degenerative dementia is Alzheimer type dementia;

(10) The nerve cell death inhibitor according to any one of (1) to (4), wherein the nerve cell death inhibitor is a prophylactic and/or therapeutic agent for cerebral infarction;

(11) The nerve cell death inhibitor according to (10), wherein the prophylactic and/or therapeutic agent for cerebral infarction is a prophylactic agent against the recurrence of cerebral infarction;

(12) A pharmaceutical composition containing a pitavastatin, donepezil or a salt thereof, and a pharmaceutically acceptable carrier;

(13) The pharmaceutical composition according to (12) above, wherein the pitavastatin is pitavastatin calcium;

(14) The pharmaceutical composition according to (12) or (13) above, wherein the salt of donepezil is donepezil hydrochloride;

(15) The pharmaceutical composition according to anyone of (12) to (14) above, wherein a preparation containing a pitavastatin and a preparation containing donepezil or a salt thereof are administered in combination;

(16) The pharmaceutical composition according to anyone of (12) to (15) above, wherein the pharmaceutical composition is intended for the inhibition of nerve cell death;

(17) The pharmaceutical composition according to anyone of (12) to (16) above, wherein the pharmaceutical composition is intended for the protection of cerebral nerves;

(18) The pharmaceutical composition according to anyone of (12) to (17) above, wherein the pharmaceutical composition is intended for the prevention and/or treatment of a demential disease;

(19) The pharmaceutical composition according to (18) above, wherein the prevention and/or treatment of a demential disease is to inhibit the progression of a demential disease;

(20) The pharmaceutical composition according to (18) or (19) above, wherein the demential disease is vascular dementia or degenerative dementia;

(21) The pharmaceutical composition according to (20) above, wherein the degenerative dementia is Alzheimer type dementia;

(22) The pharmaceutical composition according to anyone of (12) to (15) above, wherein the pharmaceutical composition is intended for the prevention and/or treatment of cerebral infarction;

(23) The pharmaceutical composition according to (22) above, wherein the prevention and/or treatment of cerebral infarction is intended for the prevention of recurrence of cerebral infarction;

(24) A method for inhibiting nerve cell death in a patient, the method including administering to the patient an effective amount of a pharmaceutical composition containing a pitavastatin, donepezil or a salt thereof, and a pharmaceutically acceptable carrier, the amount being sufficient to inhibit nerve cell death;

(25) A method for protecting cerebral nerves in a patient, the method including administering to the patient an effective amount of a pharmaceutical composition containing a pitavastatin, donepezil or a salt thereof, and a pharmaceutically acceptable carrier, the amount being sufficient to protect cerebral nerves;

(26) The method according to (24) or (25) above, wherein the pitavastatin is pitavastatin calcium;

(27) The method according to any one of (24) to (26) above, wherein the salt of donepezil is donepezil hydrochloride;

(28) The method according to any one of (24) to (27) above, wherein a preparation containing a pitavastatin and a preparation containing donepezil or a salt thereof are administered in combination;

(29) The method according to any one of (24) to (28) above, wherein the inhibition of nerve cell death or the protection of cerebral nerves is intended for the prevention and/or treatment of a demential disease;

(30) The method according to (29) above, wherein the prevention and/or treatment of a demential disease is to inhibit the progression of a demential disease;

(31) The method according to (29) or (30) above, wherein the demential disease is vascular dementia or degenerative dementia;

(32) The method according to (31) above, wherein the degenerative dementia is Alzheimer type dementia;

(33) A method for preventing and/or treating cerebral infarction in a patient, the method including administering to the patient an effective amount of a pharmaceutical composition containing a pitavastatin, donepezil or a salt thereof, and a pharmaceutically acceptable carrier, the amount being sufficient for prevention and/or treatment of cerebral infarction;

(34) The method according to (33) above, wherein the prevention and/or treatment of cerebral infarction is prevention of recurrence of cerebral infarction;

(35) Use of a combination of a pitavastatin and donepezil or a salt thereof, for the manufacture of a nerve cell death inhibitor;

(36) Use of a combination of a pitavastatin and donepezil or a salt thereof, for the manufacture of a cerebral nerve protective agent;

(37) The use according to (35) or (36) above, wherein the pitavastatin is pitavastatin calcium;

(38) The use according to any one of (35) to (37) above, wherein the salt of donepezil is donepezil hydrochloride;

(39) The use according to any one of (35) to (38) above, wherein the use of a combination of a pitavastatin and donepezil or a salt thereof is to use a preparation containing a pitavastatin and a preparation containing donepezil or a salt thereof in combination;

(40) The use according to any one of (35) to (39) above, wherein the nerve cell death inhibitor or cerebral nerve protective agent is intended for the prevention and/or treatment of a demential disease;

(41) The use according to (40) above, wherein the prevention and/or treatment of a demential disease is to inhibit the progression of a demential disease;

(42) The use according to (40) or (41) above, wherein the demential disease is vascular dementia or degenerative dementia;

(43) The use according to (42) above, wherein the degenerative dementia is Alzheimer type dementia;

(44) A use of a combination of a pitavastatin and donepezil or a salt thereof, for the manufacture of a prophylactic agent and/or therapeutic agent for cerebral infarction; and

(45) The use according to (44) above, wherein the preventive agent and/or therapeutic agent for cerebral infarction is intended for the prevention of recurrence of cerebral infarction.

EFFECTS OF THE INVENTION

According to the present invention, a nerve cell death inhibitor exhibiting an excellent nerve cell death inhibitory action can be provided, and a cerebral nerve protective agent, a progression inhibitor for a demential disease, a prophylactic and/or therapeutic agent for a demential disease, a prophylactic agent against the recurrence of cerebral infarction, and a prophylactic and/or therapeutic agent for cerebral infarction can be provided.

BRIEF DESCRIPTION OF THE DRAWINGS

FIG. 1 is a graph showing the effects of individual administrations or combined administration of pitavastatin and ARICEPT (donepezil hydrochloride) on nerve cell death.

FIG. 2 is a graph showing the effects of individual administrations or combined administration of simvastatin and ARICEPT (donepezil hydrochloride) on nerve cell death.

BEST MODE FOR CARRYING OUT THE INVENTION

The pitavastatins used in the present invention include pitavastatin and a salt thereof, and a lactone derivative of the compound or the salt, and also a solvate of these with a solvent which is acceptable as a pharmaceutical product, such as a hydrate of the compound, the salt or the lactone derivative. Pitavastatins have a cholesterol synthesis inhibitory activity based on the HMG-CoA reductase inhibitory action, and are known as a therapeutic agent for hyperlipidemia. Examples of the salt of pitavastatin include alkali metal salts such as sodium salt and potassium salt; alkaline earth metal salts such as calcium salt and magnesium salt; organic amine salts such as phenethylamine salt or ammonium salts and the like. Among these, as for the pitavastatin, a salt of pitavastatin is preferred, and a calcium salt and a sodium salt are particularly preferred.

A pitavastatin can be produced by the methods described in U.S. Pat. No. 5,856,336 and JP-A No. 1-279866.

The donepezil or a salt thereof used in the present invention are known as a therapeutic agent for Alzheimer type dementia based on the acetylcholinesterase inhibitory action, and donepezil hydrochloride can be easily produced by a known method, for example, a method disclosed in JP-A No. 1-79151, JP-A No. 07-252216, JP-A No. 11-263774, JP-A No. 11-171861, or the like. Donepezil hydrochloride can be easily obtained as a commercially available product (trade name "ARICEPT"). The salt of donepezil is not particularly limited as long as it is a pharmaceutically acceptable salt, and examples thereof include inorganic acid salts such as hydrochloride, sulfate, nitrate, hydrobromide and phosphate; organic acid salts such as acetate, trifluoroacetate, fumarate, maleate, lactate, tartrate, citrate, succinate, malonate, methanesulfonate and p-toluenesulfonate; and the like. Among these, hydrochloride is preferred.

The present invention involves administering a pitavastatin and donepezil or a salt thereof in combination. As shown in the Examples that will be described later, in a rat model for revascularization of vertebral-carotid artery occlusion (4-point ischemia), when a pitavastatin and donepezil or a salt thereof were used in combination, nerve cell death in the hippocampus CA1 region was significantly inhibited, and a marked nerve cell death inhibitory action was exhibited, in comparison to the case where the two drugs were each individually administered. Therefore, the medicament of the present invention is useful as a nerve cell death inhibitor. The nerve cell death inhibitor of the present invention is further useful as a cerebral nerve protective agent, a progression inhibitor for a demential disease, a prophylactic and/or therapeutic agent for a demential disease, a prophylactic agent against the recurrence of cerebral infarction, and a prophylactic and/or therapeutic agent for cerebral infarction. Examples of the demential disease include vascular dementias such as multi-infarct dementia extended ischemia type (including Binswanger type leukoencephalopathy), multiple cerebral infarction type, focal cerebral infarction type and hereditary vascular dementia (CADASIL, or the like); and degenerative dementias such as Alzheimer type dementia (Alzheimer's disease (AD) or senile dementia Alzheimer's type (SDAT)), frontotemporal lobar degeneration (frontotemporal dementia; FTD, Pick's disease, or the like), Lewy body type dementia (diffuse Lewy body disease (DLBD) or the like), Parkinson's disease (PD) with dementia, neurofibril variation type senile dementia, argentaffin granular dementia, Huntington's disease, progressive supranuclear palsy, and corticobasal ganglionic degeneration; as well as Creutzfeldt-Jakob disease, HIV-associated dementia, and the like. Among these demential diseases, the medicament of the present invention is particularly useful as a progression inhibitor for Alzheimer type dementia, or a prophylactic and/or therapeutic agent for Alzheimer type dementia.

The dosage form of the medicament or pharmaceutical composition used in the present invention is not particularly limited, and can be appropriately selected in accordance with the therapeutic purpose. Examples of the dosage form include oral administration by means of tablets, capsules, granules, film-coated tablets, powders, syrups or the like, and parenteral administration by means of injectable preparations, suppositories, inhalants, transdermal absorption patches, eye drops, nose drops or the like. However, usually, oral administration is preferred.

In the case of preparing an oral solid preparation, tablets, granules, powders, capsules or the like can be produced by a standard method, after adding an excipient, and if necessary, a binding agent, a disintegrant, a gliding agent, a colorant, a flavoring agent, a fragrance and the like. As such additives, those generally used in the pertinent art may be used, and examples thereof include, as the excipient, lactose, sodium chloride, glucose, starch, microcrystalline cellulose, silicic acid, and the like; as the binding agent, water, ethanol, propanol, simple syrup, gelatin solution, hydroxypropylcellulose, methylcellulose, ethylcellulose, shellac, calcium phosphate, polyvinylpyrrolidone, and the like; as the disintegrant, powdered agar, sodium hydrogen carbonate, sodium lauryl sulfate, stearic acid monoglyceride, and the like; as the gliding agent, purified talc, stearic acid salts, borax, polyethylene glycol, and the like; as the colorant, β-carotin, yellow iron sesquioxide, caramel, and the like; and as the flavoring agent, sucrose, orange peel, and the like.

In the case of preparing an oral liquid preparation, an internal liquid preparation, a syrup, an elixir or the like can be prepared by a standard method, adding a flavoring agent, a buffering agent, a stabilizer, a preservative and the like. As such additives, those generally used in the pertinent art may be used, and examples thereof include, as the flavoring agent, sucrose and the like; as the buffering agent, sodium citrate and the like; as the stabilizer, tragacanth and the like; and as the preservative, paraoxybenzoic acid ester and the like.

In the case of preparing an injectable preparation, a transdermal, intramuscular or intravenous injectable preparation can be produced by a standard method, adding a pH adjusting agent, a stabilizer, an isotonic agent, and the like. As such additives, those generally used in the pertinent art may be used, and examples thereof include, as the pH adjusting agent, sodium phosphate and the like; as the stabilizer, sodium pyrosulfite and the like; and as the isotonic agent, sodium chloride and the like.

In regard to the form of use, the medicament or pharmaceutical composition of the present invention utilizes a pitavastatin and donepezil or a salt thereof in combination, and can be used as a nerve cell death inhibitor which is synergistic as a result of administration of the two drugs, and in the form capable of obtaining the effects of protecting cerebral nerves, inhibiting the progression of Alzheimer type dementia, preventing and/or treating Alzheimer type dementia, preventing the recurrence of cerebral infarction, and preventing and/or treating cerebral infarction, without being limited to these forms of use. The pitavastatin and donepezil or a salt thereof may be administered simultaneously, or may also be administered separately at an interval. That is, as for the pitavastatin and donepezil or a salt thereof, the two drugs may be formulated into a single preparation, or the two drugs may be formulated into separate preparations and used as a set (kit).

According to the present invention, in the case of administering the two drugs in a single preparation, the mixing ratio of a pitavastatin and donepezil or a salt thereof is preferably in the range of 1:0.005 to 1:500, and more preferably in the range of 1:0.1 to 1:10, from the viewpoint of obtaining a particularly excellent synergistic effect.

Furthermore, according to the present invention, in the case of formulating the two drugs into separate preparations, the preparation containing a pitavastatin is provided as a nerve cell death inhibitor which is administered in combination with donepezil or a salt thereof, and can also be used as a cerebral nerve protective agent, a progression inhibitor for a demential disease, a prophylactic and/or therapeutic agent for a demential disease, a prophylactic agent against the recurrence of cerebral infarction, or a prophylactic and/or therapeutic agent for cerebral infarction, which is administered in combination with donepezil or a salt thereof. On the other hand, the preparation containing donepezil or a salt thereof is provided as a nerve cell death inhibitor which is administered in combination with a pitavastatin, and can also be used as a cerebral nerve protective agent, a progression inhibitor for a demential disease, a prophylactic and/or therapeutic agent for a demential disease, a prophylactic agent against the recurrence of cerebral infarction, or a prophylactic and/or therapeutic agent for cerebral infarction, which is administered in combination with a pitavastatin. The dosage forms of the two drugs may be identical or may be different. The number of administrations of the respective components may also be different.

According to the present invention, the dosage of pitavastatin may be appropriately selected in accordance with the body weight, age, gender, symptoms and the like of the patient, and usually in the case of an adult, 0.01 to 50 mg, preferably 0.1 to 20 mg, and more preferably 1 to 10 mg, may be administered per day. Furthermore, the dosage of donepezil or a salt thereof may be increased or decreased depending upon the symptoms, and in the case of an adult, 0.01 to 100 mg, preferably 0.1 to 50 mg, and more preferably 1 to 10 mg, may be administered per day. The administration may be performed once, or twice or more in divided portions in one day.

The entire description in the specification of Japanese Patent Application No. 2007-259682, which is the basic application of the present application, have been incorporated into the present specification. Furthermore, in the present specification, the expression "imbecility" in the specification of the basic application was corrected to "dementia" according to the current term.

Hereinafter, the present invention will be further described by way of Examples, but the present invention is not intended to be limited to these Examples.

Example 1

The effects of combined administration of pitavastatin calcium (hereinafter, described as pitavastatin) and donepezil hydrochloride (hereinafter, described under the trade name ARICEPT) on nerve cell death in the hippocampus CA1 region in a rat model for revascularization of vertebral-carotid artery occlusion (4-point ischemia), were evaluated according to the following testing methods.

1. Test animal and breeding environment

Seven-week old Crlj:WI male rats (Charles River Laboratories Japan Inc.) were obtained, and they were provided to the experiment after being subjected to quarantine (for 5 days) and acclimatization (for 7 days or more). Throughout the experimentation period, the rats were bred in a breeding chamber maintained under a light-dark cycle (light period under room light: 6:00 AM to 6:00 PM), at a temperature of $23\pm3°$ C. and a humidity of $55\pm15\%$, and were allowed to freely take in solid feedstuff (CRF-1; Oriental Yeast Co., Ltd.) and drinking water (tap water).

2. Preparation of solution

Pitavastatin and ARICEPT were each suspended in a 0.5% (w/v) aqueous solution of carboxymethylcellulose sodium (hereinafter, CMC-Na, SIGMA), and prepared just before use such that the amount of administration would be 5 mL/kg.

3. Testing method

The rats were divided into 5 groups (6 samples in each group) so that the average body weights were nearly uniform, and were grouped into (1) normal group (untreated group), (2) solvent control group, (3) pitavastatin (3 mg/kg) single administration group, (4) ARICEPT (0.5 mg/kg) single administration group, and (5) pitavastatin (3 mg/kg) and ARICEPT (0.5 mg/kg) combined administration group.

The day of grouping was counted as the first day of administration, and the test drug was orally administered once a day for 6 days, thus 6 times in total. The normal group and the solvent control group were administered with a 0.5% (w/v) aqueous solution of CMC-Na.

On the fifth day of administration, 35 mg/kg of pentobarbital sodium (Nembutal (registered trademark) injectable solution, Dainippon Pharmaceutical Co., Ltd.) was intraperitoneally administered to the rats excluding those in the normal group. The right and left alar foramens were exposed from the first cervical spine part under anesthesia, and the vertebral arteries were thermally solidified using a soldering iron, so as to permanently occlude the vertebral arteries on both sides. Subsequently, the common carotid arteries on both sides were exposed and peeled off, and a silicone tube was indwelling in a circular shape and sutured.

On the sixth day of administration, while the rats excluding those in the normal group were anesthetized with diethyl ether, the common carotid arteries on both sides were exposed through the indwelled silicone tube, and temporarily occluded for 10 minutes using a Sugita clip (Mizuho Ikakogyo Co., Ltd.), and the skin was sutured.

On the fifth day after the occlusion and revascularization of the common carotid arteries on both sides (for the normal group, fifth day after the final administration), the rats which had been anesthetized by a standard method were subjected to perfusion fixation using 4% paraformaldehyde (pH 7.4) and then with Bouin's fluid (pH 3.5 to 4.0), and the brains were extracted. The fixated brains were dehydrated, infiltrated and embedded in paraffin, and a section having a thickness 10 μm was produced from the vicinity of Bregma −3.3 mm. Subsequently, the section was Nissle-stained, and the right-hand side hippocampus CA1 region was photographed under an optical microscope. The number of nerve cells was counted using an image analyzer (Win ROOF V5.6, Mitani Corporation), and the length of CA1 was measured.

4. Data processing and statistic analysis

According to the following formula, the number of nerve cells per unit length was determined, and the average value and standard deviation were calculated for each group.

Number of hippocampus CA1 nerve cells (cells/mm)=Number of nerve cells of CA1 (cells)/unit length (length at the site of measurement: mm)

As for the significant difference test, a Student's t-test was performed between group (1) and group (2), and Dunnett's multiple comparison test was performed between group (2) and (3), (4) or (5). As for the significance level, a hazard rate of less than 5% was considered significant in all of the tests, and the significance level was expressed separately for the case of less than 5% ($p<0.05$) and the case of less than 1% ($p<0.01$).

The results are presented in FIG. 1. The vertical axis in FIG. 1 represents the number of nerve cells (cells/mm). In FIG. 1, the symbol ##0 indicates that a significant difference existed at $p<0.01$, while the symbol * indicates that a significant difference existed at $p<0.05$. As shown in FIG. 1, the number of nerve cells in the hippocampus CA1 region in the solvent control group was recognized to have significantly decreased as compared to the normal group.

A tendency of increase in the number of nerve cells was shown in the 3 mg/kg pitavastatin single administration group and the 0.5 mg/kg ARICEPT single administration group with respect to the solvent control group, but the result was not significant. In the 3 mg/kg pitavastatin single administration group, although there was a report of the presence of significant difference (see Non-Patent Document 9), a significant difference could not be verified in such a harsh method as in the experimental method of the present invention as described above.

On the contrary, in the combined administration group of 3 mg/kg of pitavastatin and 0.5 mg/kg of ARICEPT, a significant increase was recognized in the number of nerve cells in the hippocampus CA1 region as compared to the solvent control group, and the remarkable action and effects of the present invention in which the two drugs are used in combination, were confirmed.

Comparative Example 1

Under the purpose of verifying the action of a statin other than pitavastatin, the test was performed in the same manner using simvastatin. That is, the test animal and breeding environment, preparation of solution, testing method, data processing and statistical analysis were all carried out under the same conditions as in Example 1, except that simvastatin (15 mg/kg) was used in place of pitavastatin. Therefore, five groups of (1) normal group (untreated group), (2) solvent control group, (3) simvastatin (15 mg/kg) single administration group, (4) ARICEPT (0.5 mg/kg) single administration group, and (5) simvastatin (15 mg/kg) and ARICEPT (0.5 mg/kg) combined administration group (6 to 9 samples in each group) were used.

Simvastatin was purchased from Zhejiang Kangyu Pharmaceutical Co., Ltd. (China) and provided for the experiment.

The results are presented in FIG. 2. The vertical axis in FIG. 2 represents the number of nerve cells (cells/mm). In FIG. 2, the symbol ** indicates that a significant difference existed at $p<0.01$. As shown in FIG. 2, the number of nerve cells in the hippocampus CA1 region in the solvent control group was recognized to have significantly decreased as compared to the normal group.

A tendency of increase in the number of nerve cells was shown in the 15 mg/kg simvastatin single administration group and the 0.5 mg/kg ARICEPT single administration group with respect to the solvent control group, but the result was not significant. Furthermore, in the combined administration group of 15 mg/kg simvastatin and 0.5 mg/kg ARICEPT, although a tendency of increase in the number of nerve cells in the hippocampus CA1 region was also recognized in comparison to the solvent control group, the extent of increase was smaller than the respective cases of single administration, and the action and effects of using the two drugs in combination could not be confirmed.

INDUSTRIAL APPLICABILITY

The present invention is to provide a nerve cell death inhibitor which exhibits an excellent nerve cell death inhibitory action even under extremely harsh conditions such as those in a rat model for revascularization of vertebral-carotid artery occlusion (four-point ischemia), and the invention can provide a medicament useful as a cerebral nerve protective agent, a progression inhibitor of a demential disease, a prophylactic and/or therapeutic agent for a demential disease, a prophylactic agent against the recurrence of cerebral infarction, and a prophylactic and/or therapeutic agent for cerebral infarction. Thus, the present invention has industrial applicability in the pharmaceutical industry.

The invention claimed is:

1. A nerve cell death inhibitor, comprising:
   a pitavastatin, and
   donepezil or a salt thereof.

2. The nerve cell death inhibitor according to claim 1, wherein the pitavastatin is pitavastatin calcium.

3. The nerve cell death inhibitor according to claim 1, wherein the salt of donepezil is donepezil hydrochloride.

4. A method of inhibiting nerve cell death in a patient, the method comprising:
   administering to the patient in need thereof an effective amount of a pharmaceutical composition containing (i) pitavastatin, (ii) donepezil or a salt thereof, and (iii) a pharmaceutically acceptable carrier, the amount being sufficient to inhibit nerve cell death.

5. The method according to claim 4, wherein the pitavastatin is pitavastatin calcium.

6. The method according to claim 5, wherein the salt of donepezil is donepezil hydrochloride.

7. The method according to claim 6, wherein the pitavastatin and the donepezil or the salt thereof are administered simultaneously.

8. A method of protecting cerebral nerves in a patient, the method comprising:
   administering to the patient in need thereof an effective amount of a pharmaceutical composition containing (i) pitavastatin, (ii) donepezil or a salt thereof, and (iii) a pharmaceutically acceptable carrier, the amount being sufficient to protect cerebral nerves.

9. The method according to claim 8, wherein the pitavastatin is pitavastatin calcium.

10. The method according to claim 9, wherein the salt of donepezil is donepezil hydrochloride.

11. The method according to claim 10, wherein the pitavastatin and the donepezil or the salt thereof are administered simultaneously.

12. A method of inhibiting progression of a demential disease in a patient, the method comprising:
    administering to the patient in need thereof an effective amount of a pharmaceutical composition containing (i) pitavastatin, (ii) donepezil or a salt thereof, and (iii) a pharmaceutically acceptable carrier, the amount being sufficient to inhibit progression of the demential disease.

13. The method according to claim 12, wherein the pitavastatin is pitavastatin calcium.

14. The method according to claim 13, wherein the salt of donepezil is donepezil hydrochloride.

15. The method according to claim 14, wherein the pitavastatin and the donepezil or the salt thereof are administered simultaneously.

16. A method of inhibiting a recurrence of cerebral infarction in a cerebral infarction patient, the method comprising:
    administering to the patient in need thereof an effective amount of a pharmaceutical composition containing (i) pitavastatin, (ii) donepezil or a salt thereof, and (iii) a pharmaceutically acceptable carrier, the amount being sufficient to prevent a recurrence of cerebral infarction.

17. The method according to claim 16, wherein the pitavastatin is pitavastatin calcium.

18. The method according to claim 17, wherein the salt of donepezil is donepezil hydrochloride.

19. The method according to claim 18, wherein the pitavastatin and the donepezil or the salt thereof are administered simultaneously.

* * * * *